(12) United States Patent
Algotsson et al.

(10) Patent No.: US 7,060,776 B2
(45) Date of Patent: Jun. 13, 2006

(54) MONOMERS USEFUL IN THE PREPARATION OF SEPARATION MATRICES

(75) Inventors: Mattias Algotsson, Uppsala (SE); Bengt Bjellqvist, Uppsala (SE); Ronnie Palmgren, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 10/499,884

(22) PCT Filed: Dec. 17, 2002

(86) PCT No.: PCT/SE02/02351

§ 371 (c)(1), (2), (4) Date: Dec. 27, 2004

(87) PCT Pub. No.: WO03/055923

PCT Pub. Date: Jul. 10, 2003

(65) Prior Publication Data

US 2005/0113539 A1 May 26, 2005

(30) Foreign Application Priority Data

Dec. 21, 2001 (SE) .................................... 0104386

(51) Int. Cl.
*C08F 226/02* (2006.01)

(52) U.S. Cl. ................ 526/307.3; 526/304; 526/307.2; 526/307.4; 526/307.5; 526/332

(58) Field of Classification Search ................ 526/304, 526/307.2, 307.3, 307.4, 307.5, 310, 332; 428/375, 500

See application file for complete search history.

(56) References Cited

FOREIGN PATENT DOCUMENTS

| JP | 60-190746 | * 9/1985 |
|---|---|---|
| WO | WO97/16462 | 5/1997 |

OTHER PUBLICATIONS

Saito, Noboru, et al., "Synthesis and Hydrophilicity of Multifunctionality Hydroxylated Poly(acrylamides)" Macromolecules, vol. 29, 1996 pp. 313-319.

* cited by examiner

Primary Examiner—Helen L. Pezzuto
(74) Attorney, Agent, or Firm—Yonggang Ji

(57) ABSTRACT

The invention relates to an acrylic monomer defined by formula (I):

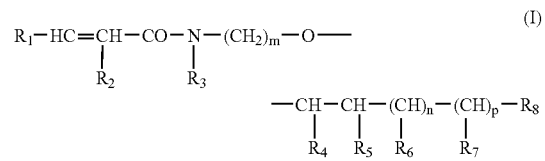

wherein
$R_1$, $R_2$ and $R_3$ are H or $CH_3$;
$R_4$ and $R_5$ are H or OH;
$R_6$ and $R_7$ are H or OH;
$R_8$ is H or $CH_3$;
m is 2–4; and
n and p are 0 or 1.

The invention also relates to a polymer comprised of repeated such monomer units as well as a separation matrix prepared thereof.

9 Claims, 2 Drawing Sheets

MONOMERS USEFUL IN THE PREPARATION OF SEPARATION MATRICES

This application is a filing under 35 U.S.C. § 371 and claims priority to international patent application number PCT/SE02/02351 filed Dec. 17, 2002, published on Jul. 10, 2003 as WO 03/055923 and also claims priority to patent application number 0104386-8 filed in Sweden on Dec. 21, 2001; the disclosures of which are incorporated herein by reference in their entireties.

TECHNICAL FIELD

The present invention relates to a novel class of monomers especially useful in the preparation of matrices for electrophoretic and chromatographic separation methods. More specifically, the present invention relates to a crosslinked matrix, which exhibits improved properties in certain conditions.

BACKGROUND

The interest of biomolecules, such as proteins, peptides and nucleic acids, has increased dramatically during the past decades. Many drugs are these days based on proteins or peptides, and an increasing number thereof are produced by biotechnological methods using recombinant DNA technology. This kind of methods requires reliable procedures for purification of the product, e.g. from cell debris and undesired substances present in the production system. In addition, studies within the field of proteomics, wherein the function and structure of a protein is explored, also requires purified protein products. The commonly used methods for separation of biomolecules are based either one or both of two principles, namely chromatography and electrophoresis. While chromatography is generally used for preparative purification of biomolecules, electrophoresis is the most powerful technique for analysis of the molecules in crude samples and at various stages of a purification procedure.

In electrophoresis, substances are separated according to their size, or based on differences in pI, as in isoelectric focusing. Polyacrylamide gels are the most widely used in the context of isoelectric focusing, since they have a higher resolving power than e.g. agarose gels. Since the chemical nature of acrylamide renders it unpleasant to handle, precast gels are in general preferred before casting in place. However, the precast gels will need to fulfill certain criteria as regards e.g. stability and shelf life. It is a generally known problem that precast polyacrylamide gels age in alkaline conditions, resulting in a decreased mobility of biological macromolecules therein and also the resolution will deteriorate. The short shelf life of precast polyacrylamide gels is primarily attributed to the hydrolytic degradation of acrylamide moieties in the gel, while the cross-linking units are relatively stable.

WO 97/16462 (Righetti et al) suggests N-mono- and di-substituted hydroxyethoxyethyl-(meth)acrylamides and their analogues in electrophoretic gels. However, it has later been shown that one of the illustrative monomers, denoted HEEAA, tends to auto-polymerise during storage as a 50% aqueous solution at 4° C., even in the presence of a free radical inhibitor. Accordingly, this group of compounds does not fulfill the need of improved and more stable matrix materials.

SUMMARY OF THE PRESENT INVENTION

One object of the present invention is to provide a separation matrix which is stable or essentially stable to hydrolysis at elevated pH values, such as above pH 10. A specific object of the invention is to provide such a matrix, which comprises a pH gradient within a range of above about pH 8.

Accordingly, another object is to provide a polymer useful to produce such a separation matrix. Thus, yet another object is to provide a monomer, which is readily, polymerisable into such polymers.

One or more of the objects above can be achieved as defined in the appended claims. Other objects and advantages will appear from the detailed description that follows.

DETAILED DESCRIPTION OF THE INVENTION

Figure 1:
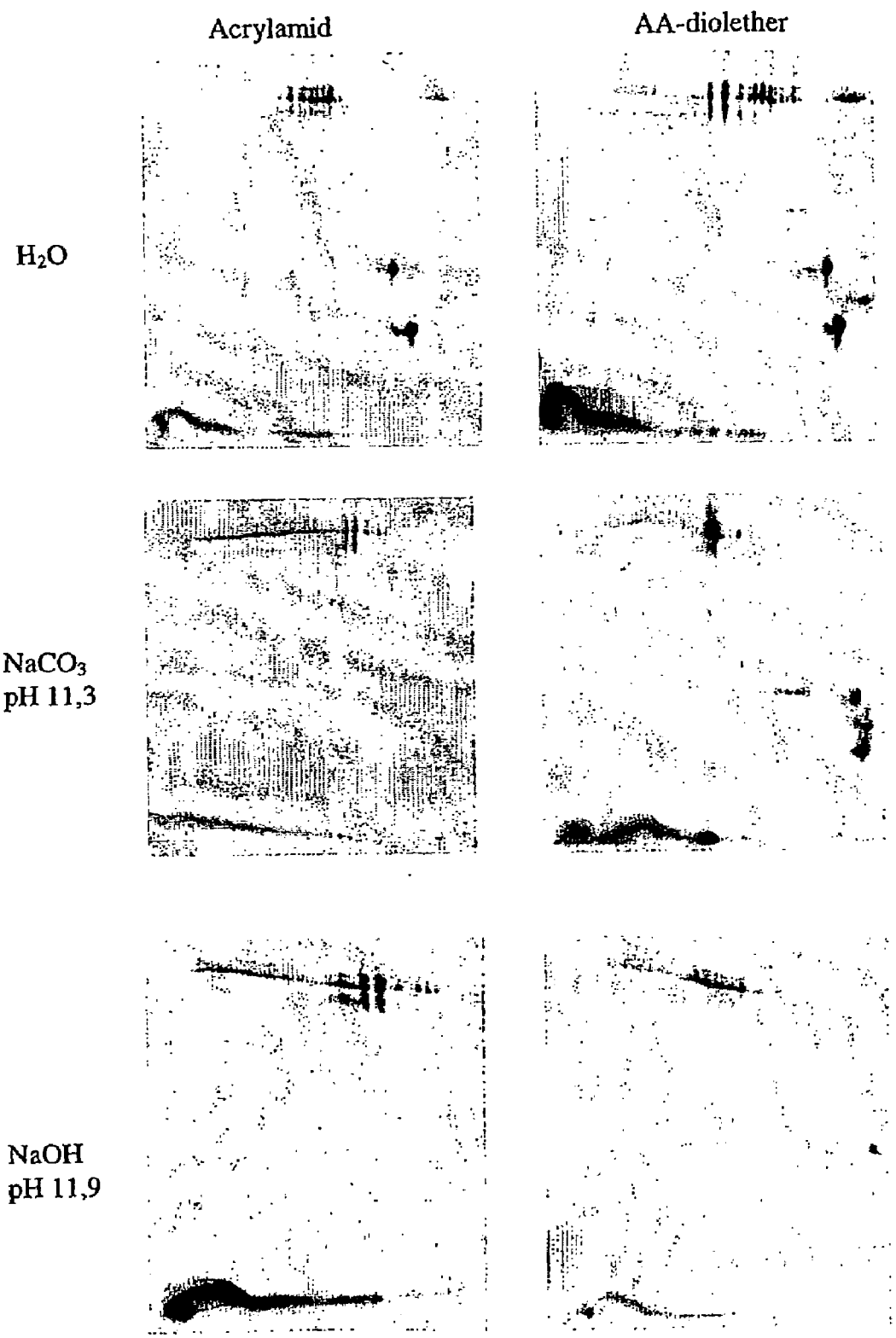
FIG. 1 shows 2D maps resulting from IPG strips (pH 6–11), treated for 60 minutes in solutions of varying pH.

A first aspect of the present invention is an acrylic monomer for use in electrophoresis, which monomer is defined by the following formula (I)

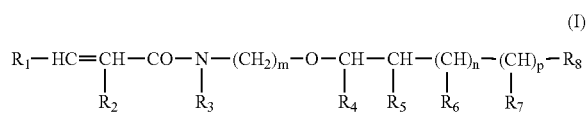

(I)

$$R_1-HC=CH-CO-N-(CH_2)_m-O-CH-CH-(CH)_n-(CH)_p-R_8$$
with substituents $R_2$, $R_3$, $R_4$, $R_5$, $R_6$, $R_7$ wherein $R_1$, $R_2$ and $R_3$ are each H or $CH_3$, respectively;

$R_4$ and $R_5$ are each H or OH, respectively;

$R_6$ and $R_7$, if present, are each H or OH, respectively, with the proviso that at least two of $R_4$, $R_5$, $R_6$ and $R_7$ are OH;

$R_8$ is H or $CH_3$, respectively;

m is an integer of 2–4; and n and p are each integers of 0 or 1, with the proviso that if n is 0, then $R_6$ is not present, and if p is 0, the $R_7$ is not present. As is easily realised, the acrylic monomer should be of sufficient purity to form a reproducible matrix suitable for such use.

$R_1$ and $R_8$ are normally H, but can alternatively be $CH_3$-groups. Each one of $R_2$ and $R_3$ can be either a H or a $CH_3$-group. The value of the integer m has not proved to be essential for the properties of the monomer, but can be selected due to starting reagents available for synthesis, or simply to match a commercially available compound. It is understood that the more OH-groups present in the monomer, the more sugar character will the product have. The present inventors has unexpectedly shown that the presence of two OH-groups instead of one improves the base stability of the monomer and products thereof, and therefore at least two of $R_4$, $R_5$, $R_6$ and $R_7$ are OH-groups according to the present invention. Depending on the values of the integers n and p, i.e. the length of the carbon chain, said two OH-groups can be located either adjacent to or distanced from one another by one or more carbon groups. This, in one advantageous embodiment, the present monomer is defined by formula (I) above, wherein $R_4$ and $R_5$ are OH-groups. In a preferred embodiment, $R_1$, $R_2$ and $R_3$ are H; the integer m is 3, n is 1 and p is 0, and accordingly $R_7$ is not present; $R_4$ is H; $R_5$ and $R_6$ are OH-groups; and $R_8$ is H. Accordingly, in this embodiment, the monomer is acrylamidopropyl-2,3-dihydroxypropylether, which for example can be synthesised as described in example 1 below.

A second aspect of the present invention is a process of preparing an acrylic monomer as described above, which comprises activating the carbonyl carbon of an acryloyl or methacryloyl derivative according to any conventional method, reacting the activated product with the amino group of an aminoalkyl-hydroxy alkyl ether, and subjecting the reaction products to an ion exchange treatment sufficient to remove substantially all of the charged polymerisable compounds therefrom. As the skilled person in this field realises, there are various ways to protect the hydroxy groups during the activation reaction. It can for example be by forming a ketal, such as a solketal. In the experimental part below, one illustrative way of synthesising a monomer according to the invention will be provided.

The present monomer can be prepared in sufficient purity to form a reproducible matrix suitable for use in electrophoresis. Thus, depending on the method used for synthesis, the skilled person in this field can easily choose a suitable method of purification. Naturally, the desired purity will depend on the intended use. For example, the first dimension of a 2D-electrophoresis requires a high degree of purity, such as above 99%. Accordingly, a matrix, such as a gel, produced from the present monomer can be essentially free from undesired contaminants remaining from the synthesis thereof. A further advantage of the present invention in this context is that it has not shown any tendency to autopolymerise, which as mentioned above has been a problem with the prior art.

Yet another advantage with matrices produced according to the present invention is based on the unexpected founding that the texture thereof differs from prior art matrices. Usually, in order to prevent cracking of the gel during storage and handling, a softening agent, such as glycerol, is added. However, the present gel can be stored and handled without cracking even without such a glycerol addition. This is an important advantage, since in some applications it is desired to avoid the presence of softening agents. For example, if it is envisaged to run mass spectrometry (MS) after only the first dimension of a conventional 2D separation, then it is much desired to avoid any unnecessary additives to achieve best results.

A third object of the invention is a polymer comprising repeating units of at least one monomer as defined by formula (I). In a specific embodiment, the present polymer comprises repeating units of a single one of the monomers defined by formula (I). In one embodiment, the present polymer is internally cross-inked by a cross-linking monomer having at least two ethylenic double bonds.

The monomers according to the present invention can be polymerised by a free radical polymerisation using any conventional initiator well known in this field, such as peroxides, 2,2'-azo-bis-isobutyronitrile, N,N,N',N'-tetramethyiethylenediamine plus ammonium or alkali metal persulphate. Some initiators requires irradiation, for example by UV light, in order to provide the initiation. Redox systems can also be used, such as Fenton's reagent. Polymerisation can alternatively be initiated by electron beam irradiation or γ-irradiation. The polymerisation can be a homopolymerisation, a copolymerisation, an emulsion polymerisafion or a suspension polymerisation, all of which are well known methods in this field. Thus, e.g. for emulsion polymerisation, the monomer solution is dispersed and polymerised in the form of droplets in another phase, which is not a good solvent for the monomer.

The monomers may be polymerised either alone or with other compounds and materials having one or more polymerisable double bonds.

Accordingly, a fourth aspect of the present invention is a cross-linked aqueous matrix, such as a gel, comprising a water-insoluble copolymer comprising repeating units of the monomer defined by formula (I). Such a matrix can be comprised on just the one monomer as defined by formula (I) or a mixture thereof with one or more other suitable monomers. Such monomers can e.g. be selected within a wide range of compound known and commonly used for separation matrices.

In one embodiment of the present matrix, the cross-linker is for example bisacrylamide, piperazinacrylamide, poly (ethylene glycol) dimethacrylate.

In a specific embodiment, which is especially suitable for use at high pH values, the matrix according to the invention is comprised of a mixture of the monomer defined by formula (I) above and a monomer defined by the following formula (II)

$$—(NH)_tC(=NH)NH_2) \qquad (II).$$

Individual groups of formula (I) may be in protonated (charged) form or in unprotonated (uncharged) form. The anchoring of the groups to the carrier material may be via a linker according to techniques well known to the skilled in this field. t is an integer of 0 or 1. As the skilled person will realise, the hydrogens can be replaced by suitable substituents.

In an advantageous embodiment, the monomer defined by formula (II) is agmatine. In the experimental part below, the synthesis of acrylamidoagmatine will be described together with the polymerisation thereof.

An advantageous embodiment of the matrix according to the invention is comprised of about 3–8% of the polymer defined by formula (I) and crosslinker in amounts required for formation of a gel and the monomer defined by formula (II), such as acrylamidoagmatine. The latter chemical is than added to the matrix generating solution in a concentration following in the region 1 and 40 mM. Normally the concentration of the latter compound is allowed to vary from one end of the matrix to the other as this compound together with other monomers containing acidic and basic groups will determine the pH resulting within the matrix.

As mentioned above, the monomer according to the present invention has surprisingly been shown to provide matrices i.e. gels that are unexpectedly stable to basic pH values.

By "stable to basic pH values" is meant herein that the gel is sufficiently stable to be used during all steps of an electrophoretic procedure. The present matrices are especially advantageous for use in isoelectric focusing, which is often the first step of a conventional 2D separation. An especially advantageous embodiment of this aspect of the invention is a matrix, which is suitable for use in the pH range above about 9.

In one embodiment, the present matrix has been functionalized with pH-buffering groups. Any known form of pH-buffering groups can be used to this end, and methods of functionalizing a matrix such as the present with functional groups is easily performed by the skilled n this field according to well known methods. Accordingly, a matrix according to the invention can comprise one or more kinds of functional groups.

In an advantageous embodiment, the present matrix comprises a pH gradient, which includes pH values higher than 9. This includes wide gradients, such as pH 3–12, pH 6–11, and 7–12, where an notable and maybe a major fraction of the pH fraction falls below pH 9, but also more narrow range gradients, which extend to pH values above 9, such as pH 9–12, pH 9–11, pH 9–10, pH 8,5–9,5 and pH 9,5–10.

In one embodiment, the pH-buffering groups used to functionalize the present matrix exhibit pKa values of above about 10. pKa values referred to herein are measured in aqueous solutions (25° C.) for a low molecular compound/monomer which has the particular functionalizing group present and at least partly bound to the base skeleton of the matrix. The pKa values have been extrapolated to ionic strength zero. (See e.g. Handbook of Chemistry and Physics, 56$^{th}$ edition (1975–1976) page D-133, CRC Press, 18901 Cranwood Parkway, Cleveland, OH, U.S.A)

The matrix according to the invention can be prepared in virtually any desired form or shape. Thus, in one embodiment, the present matrix has been polymerised in a mold and can be used in that mold for electrophoretic separation. In another embodiment, the matrix is in the form of a sheet, a rod or a thin filament. In a specific embodiment, the present matrix according has been grafted onto a solid support, such as a plastic or glass material. In the most advantageous embodiment, the present matrix is a gel strip comprised of gel grafted to a plastic support.

A fourth aspect of the present invention is a method of isolating molecules, which comprises subjecting such molecules to electrophoresis. The present matrix is the used as separation medium and contacted with the molecule to be separated. The molecule to be separated is migrating as an ionic species in said medium.

In an advantageous embodiment, the separated species is transferred to another material wherein it is subject to a size-based separation. Accordingly, the present invention can advantageously be used as the first, electrophoretic step in a conventional 2D separation.

DETAILED DESCRIPTION OF THE DRAWINGS

FIG. 1 shows 2D maps resulting from IPG strips (pH 6–11), treated for 60 minutes in solutions of varying pH. Acrylamide is shown to the left of the picture, while the term "AA-diolether" as shown to the right is an abbreviation of the illustrative acrylamidopropyl-2,3-dihydroxypropylether according to the invention. From top to bottom, the pictures show H$_2$O, NaCO$_3$ (pH 11.3), and NaOH (pH 11.9).

Figure 2:
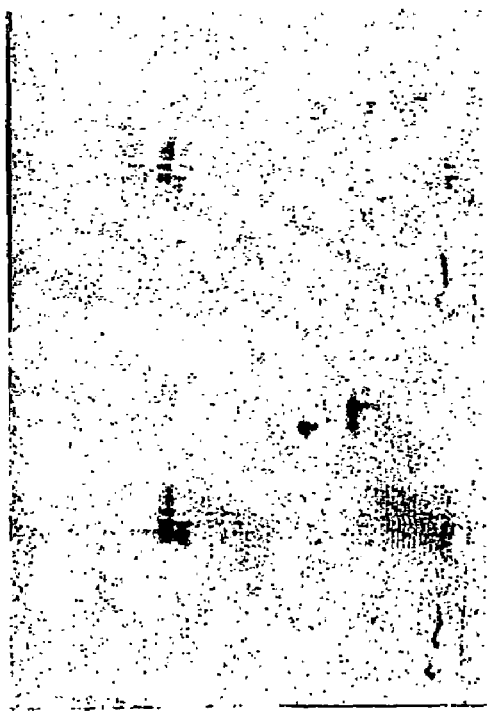
FIG. 2 shows 2D maps resulting from IPG strips (pH 6–11), focused for varying times.
Figure 2:
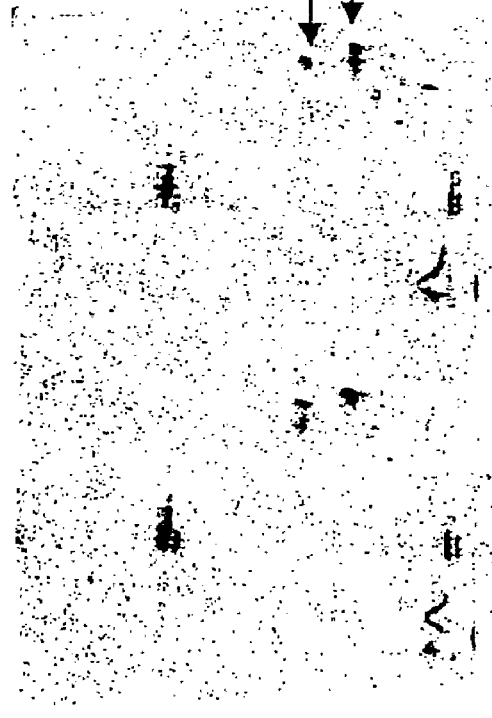

FIG. 2 shows 2D maps resulting from IPG strips (pH 6–11), focused for varying times. Acrylamide is shown above and AA-diolether, while the focussing time to the left was 3 hours and 40 minutes and that to the right 24 hours. The upper arrow in the lower picture to the right shows the location of the histon H2B, turkey, while the arrow below shows the location of the alkylated lysozyme, as discussed in example 2 below.

EXPERIMENTAL PART

The examples shown below are only for illustrative purposes and are not intended to limit the present invention as defined by the appended claims. All references given below and elsewhere in the present application are hereby included herein by reference.

Example 1

Synthesis of Acrylamidopropyl-2,3-dihydroxypropylether

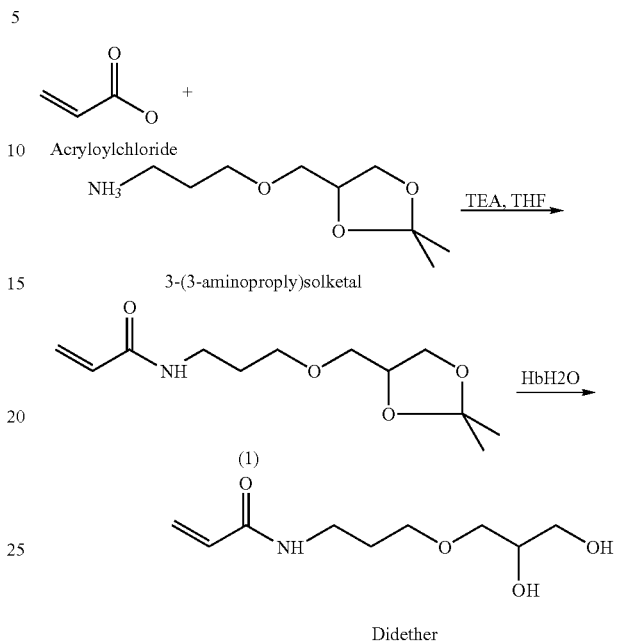

3-(3-aminopropyl)solketal (10 g, 57 mmol) was weighed into a three-necked beaker and dissolved in THF (200 ml) during magnetic stig. Triethylamine (9.8 ml, 70 mmol) was added and the solution was cooled to 0° C. (ice-bath). Acryloylchloride (5.7 ml, 70 mmol) was added dropwise and carefully through a dropping-funnel. A white salt immediately precipitated. After the addition the solution was allowed to regain RT and was left to react for three hours during magnetic stirring. The reaction was followed with TLC (developed in EtOAc/methanol 9:1). The salt was filtered off on a glass-filter (p4) and the solution was kept in the fridge over night. The solvent was evaporated off on a rotary evaporator and the product (pale yellow oil) was purified with flash-chromatography (EtOAc/methanol gradient from 0% to 10% methanol). Product fractions was identified with TLC, evaporated and dried over night in vacuum (RT, 0.1 mbar) to give a colourless oil (10.9 g, 45 mmol, 79% yield).

The oil was dispersed in distilled water (30 ml) and deprotected with DOWEX (washed with distilled water beforehand). The solution was left stirring for about four hours and the reaction was followed with TLC (EtOAc/MeOH 9:1). The DOWEX was filtered off on a glass-filter (p4) packed with Celite to give a clear colourless solution (40 ml, 1M-solution, 70% overall yield).

Example 2

Stability at High pH Values of an acrylamidopropyl-2,3-dihydroxypropylether (AA-diolether) Based Matrix To control the stability of IPG strips pH 6–11, strips have been generated with acrylamide and with the AA-diolether in a manner analogous to what is described in Gorg A, Postel W, Gunther S: "The current state of two-dimensional electrophoresis with immobilized pH gradients" Electrophoresis. 1988 Sep;9(9):531–46. Review. Briefly gels were casted in cassettes of the dimensions 250×100×0.5 mm on a plastic backing. The reference acrylamide gel was generated from two solutions; one "acidic" heavy solution containing 48.5 gram acrylamide/litre; 1.5 gram bisacrylamide/litre; 20% glycerol and a mixture of Immobiline™ (Amersham Biosciences AB, Uppsala, Sweden) chemicals giving a resulting pH of 6 in the generated gel, but prior to polymerisation titrated with Tris to pH 7 and a second "basic" light solution containing 48.5 gram acrylamide/litre; 1.5 gram bisacrylamide/litre; 20% glycerol and a mixture of Immobiline™ chemicals giving a resulting pH of 11 in the generated gel, but prior to polymerisation titrated with acetic acid to pH 7. For the gel casting 8 ml of each type of solution was used and prior to the casting the catalysts were added (20 µl of a solution containing 20% ammoniumpersulphate and 20 µl of a solution containing 20% tetramethyl ethylene diamine). A conventional device for gradient generation was used and the mould was filled with a solution giving a linear gradient starting at pH 6 and 20% glycerol and ending at pH 11 and 0% glycerol. The gel was allowed to polymerise for 1 hour at 50° C. In the gel to be tested, acrylamide was substituted with 5.85 gram AA-diolether/litre in the two solutions used for gel casting.

After polymisation, the gels were taken out of the cassettes and washed in distilled water for 4× 15 minutes to wash out Tris, acetic acid, glycerol and non-incorporated monomers from the gels. For the gel produced with acrylamide 1% of glycerol was added in the final washing step in order to avoid cracking of the gel in the drying step to follow. After washing, the gels were allowed to dry at room temperature overnight and the dried gels were then cut into 3.3 mm wide strips, which were kept in freezer at −18° C. until use.

The base stability was tested by treating strips in either water, sodium carbonate solution pH 11.3 or 0.01 M NaOH pH 11.9 for 60 minutes, followed by washing and drying of the strips with the procedure described above. Prior to focusing, the strips were reswollen in a solution containing 8 M urea, 2% w/v 3-[(3-cholamidopropyl)dimethylammonio]-1-propanesulphonate (CHAPS), 65 mM dithiothreitol (DTT) and 0.5% v/v IPG buffer pH 6–11. FIG. 1 shows resulting 2D maps generated with 10 cm long strips made with acrylamide and AA-diolether, respectively, and focused for 4 hours and 30 minutes (gradient from 500V to 3500 V for 1 hour 30 min followed by 3 hours focusing at 3500 V giving a total of 13.5 kilovolt hours) with a mixture of turkey histones and alkylated lysozyme as sample. The turkey histones were prepared as described in Csordas A, Pedrini M. Grunicke H. "Suitability of staining techniques for the detection and quantitation of nonhistone high mobility group proteins" Electrophoresis. 1990 Feb;11 (2):118–23, while the alkylated lysozyme were made by dissolving 20 mg lysozyme from Sigma in 1 mL 3% SDS in a 2 mL Eppendorff tube. 20 mg DTT was added and the sample was kept at 95° C. for 5 min. After cooling, 0.3 mL 30% acrylamide was added, sample was mixed and incubated for 1 h at room temperature. The sample was divided into two 1 ml aliquots and 1 ml of a freshly prepared EtOH/HAc mixture (80/20) was added to each aliquot to precipitate the lysozyme. The precipitate was spun down and washed with a solution containing 40% EtOH and 10% HAc two times and finally with 40% EtOH. Both samples were solved in sample solution (8M urea, 4% w/v CHAPS, 65 mM DTT and 2% v/v IPG buffer pH 3–10 NL). For the acrylamide based strips spot positions have, as a result of washing at high pH, shifted towards the cathode and the most basic spots have disappeared compared to the result given by the water treated strip. With the AA-diolether strips no obvious shifts of spots towards the cathode can be seen as a result of the treatment at high pH Example 3

Synthesis of Acrylamidoagmatine and Polymerisation thereof Synthesis

Agmatine sulphate was desalted with barium hydroxide in water, barium sulphate which was formed precipitated in water and was filtered off. Agmatine (50 mmol) was dissolved in methanol and diisoproylamine (55 mmol) was added, the solution was cooled to 0° C. with an ice/water bath. 60 mmol acryloylchloride was added over a period of time (30 min) while the solution was kept at 0° C. Then the reaction solution was allowed to reach room temperature over night. The solvent was evaporated and the product was purified with flash chromatography on an RPC-18 column with a water/methanol gradient.

Polymerisation:

Acrylamidoagmatine (AAA) was homopolymerised and copolymerised with acrylamide (AA) and acrylamidopropanol (AAP) in water, with APS (ammonium persulphate)/Temed) redox system as initiator.

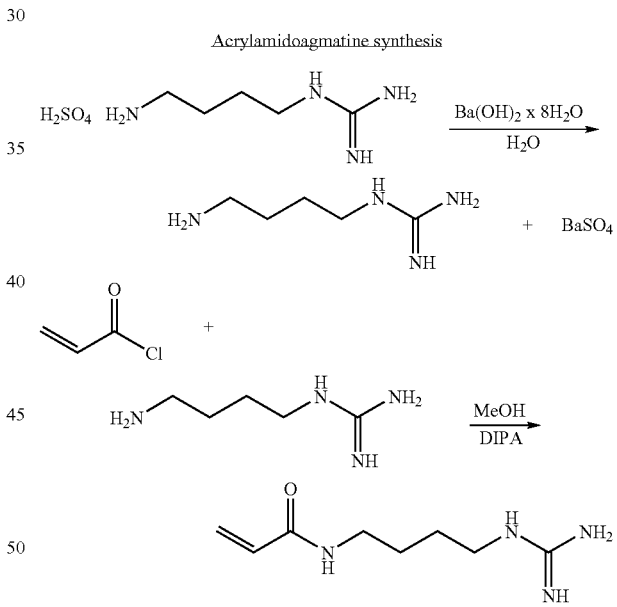

TABLE 1

| Monomer conc % | [M] | [APS] mM | [Temed] mM | Water µl | AAA ML | AA mL | AAP mL |
|---|---|---|---|---|---|---|---|
| 6% | 0.83 | 3.25 | 4.5 | 1143.6 | 2.8 | 0 | 0 |
| 8% | 1.1 | 3.25 | 4.5 | 243.6 | 3.7 | 0 | 0 |
| 6% | 0.83 | 3.25 | 4.5 | 1143.6 | 1.4 | 1.4 | 0 |
| 8% | 1.1 | 3.25 | 4.5 | 243.6 | 1.85 | 1.85 | 0 |
| 6% | 0.83 | 3.25 | 4.5 | 1143.6 | 1.4 | 0 | 1.4 |
| 8% | 1.1 | 3.25 | 4.5 | 243.6 | 1.85 | 0 | 1.85 |

The copolymer made with AAP is much more stable against basic hydrolysis than the co-polymer with AA

What is claimed is:

1. A cross-linked aqueous matrix comprising a water-insoluble copolymer comprising repeating units of an acrylic monomer suitable for use in electrophoresis, comprising the general formula

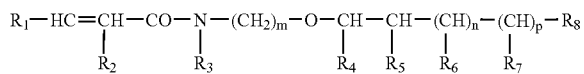

(I)

wherein
$R_1$, $R_2$ and $R_3$ are each H or $CH_3$, respectively;
$R_4$ and $R_5$ are each H or OH, respectively;
$R_6$ and $R_7$, if present, are each H or OH, respectively, with the proviso that at least two of $R_4$, $R_5$, $R_6$ and $R_7$ are OH;
$R_8$ is H or $CH_3$, respectively;
m is an integer of 2–4; and
n and p are each integers of 0 or 1 with the proviso that if n is 0, then $R_6$ is not present, and if p is 0, the $R_7$ is not present;
said matrix further comprising a mixture of the monomer defined by the general formula (II)

—(NH)$_t$C(=NH)(NH$_2$)     (II)

wherein t is an integer of 0 or 1,
together with other monomers containing acidic and basic groups to determine the pH resulting within the matrix.

2. The matrix of claim 1, wherein the monomer defined by formula (II) is agmatine.

3. The matrix of claim 1, further comprising functionalizing pH-buffering groups.

4. The matrix of claim 3, wherein said pH-buffering groups exhibit pKa values of above about 9.

5. The matrix of claim 1, which includes a pH gradient of from about 6–12.

6. The matrix of claim 1, which has been polymerised in a mold for use in electrophoretic separation.

7. The matrix of claim 1, which is in the form of a sheet, a rod or a thin filament.

8. The matrix of claim 1, which has been grafted onto a solid support, such as a plastic or glass support.

9. The matrix of claim 1, wherein the repeating units have been cross-linked with bis-acrylamide.

* * * * *